United States Patent
Lee et al.

(10) Patent No.: US 9,152,150 B1
(45) Date of Patent: Oct. 6, 2015

(54) COMPOSITIONS, SYSTEMS, AND METHODS FOR IMMISCIBLE FLUID DISCRETE VOLUME MANIPULATION

(75) Inventors: Linda G. Lee, Palo Alto, CA (US);
Mark F. Oldham, Los Gatos, CA (US);
Sam L. Woo, Redwood City, CA (US);
David M. Cox, Foster City, CA (US);
Richard T. Reel, Hayward, CA (US);
Peter N. Ma, Cupertino, CA (US); Ben F. Johnson, Palo Alto, CA (US); Dennis Letho, Santa Clara, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 883 days.

(21) Appl. No.: 12/036,037

(22) Filed: Feb. 22, 2008

Related U.S. Application Data

(60) Provisional application No. 60/891,225, filed on Feb. 22, 2007, provisional application No. 60/891,208, filed on Feb. 22, 2007.

(51) Int. Cl.

| | |
|---|---|
| *G05D 11/00* | (2006.01) |
| *G05D 7/06* | (2006.01) |
| *B01L 3/00* | (2006.01) |
| *B01F 13/00* | (2006.01) |
| *G01N 35/08* | (2006.01) |
| *B01L 3/02* | (2006.01) |

(52) U.S. Cl.
CPC .......... *G05D 7/0694* (2013.01); *B01F 13/0071* (2013.01); *B01F 13/0072* (2013.01); *B01L 3/0265* (2013.01); *B01L 3/502784* (2013.01); *G01N 35/08* (2013.01); *B01L 2200/0605* (2013.01); *B01L 2200/0673* (2013.01)

(58) Field of Classification Search
CPC ........... B01L 3/0265; B01L 3/502784; B01L 2200/0605; B01L 2200/0673; B01F 13/0071; B01F 13/0072; G01N 35/08; G05D 7/0694
USPC .......... 137/114, 896, 897, 88; 422/82; 436/53
See application file for complete search history.

(56) References Cited

U.S. PATENT DOCUMENTS

| | | | | |
|---|---|---|---|---|
| 4,253,846 | A | * 3/1981 | Smythe et al. | 436/53 |
| 4,908,112 | A | 3/1990 | Pace | |
| 5,092,972 | A | 3/1992 | Ghowsi | |
| 5,134,079 | A | * 7/1992 | Cusack et al. | 436/53 |
| 5,149,658 | A | * 9/1992 | Cassaday et al. | 436/53 |
| 5,739,036 | A | * 4/1998 | Parris | 436/53 |
| 5,843,767 | A | 12/1998 | Beattie et al. | |
| 5,884,649 | A | * 3/1999 | Proudman | 137/7 |
| 5,961,800 | A | 10/1999 | McBride et al. | |
| 6,485,905 | B2 | 11/2002 | Hefti | |
| 6,508,273 | B1 | 1/2003 | Van Den Berg | |

(Continued)

OTHER PUBLICATIONS

European Application No. 06802016.3, Extended European Search Report mailed on Nov. 3, 2010.
Chiou, J. et al., "A Closed-Cycle Capillary Polymerase Chain Reaction Machine", *Analytical Chemistry, American Chemical Society*, vol. 73, No. 9, 2001, 2018-2021.

(Continued)

*Primary Examiner* — Kevin Murphy

(57) ABSTRACT

Systems and methods of manipulating discrete volumes of a first fluid in a second fluid are provided. In some embodiments, discrete volumes can be formed in a conduit. In other embodiments, addition fluid can be added to a discrete volume in a first conduit by injecting the addition fluid at a relatively higher pressure. In some embodiments, discrete volumes that normally would not coalesce can be manipulated to be merged together.

8 Claims, 13 Drawing Sheets

FIG.3

(56) References Cited

U.S. PATENT DOCUMENTS

| | | |
|---|---|---|
| 6,626,416 B2 | 9/2003 | Sharma et al. |
| 6,719,535 B2 | 4/2004 | Rakestraw et al. |
| 6,908,770 B1 * | 6/2005 | McDevitt et al. ............ 436/518 |
| 7,041,481 B2 | 5/2006 | Anderson |
| 7,955,864 B2 | 6/2011 | Cox et al. |
| 2001/0049148 A1 | 12/2001 | Wolk et al. |
| 2003/0006140 A1 | 1/2003 | Vacca et al. |
| 2003/0162213 A1 | 8/2003 | Fuller et al. |
| 2003/0194709 A1 | 10/2003 | Yang |
| 2003/0199081 A1 | 10/2003 | Wilding et al. |
| 2004/0058450 A1 | 3/2004 | Pamula et al. |
| 2004/0241721 A1 | 12/2004 | Gjerde et al. |
| 2004/0248144 A1 | 12/2004 | Mir |
| 2005/0130173 A1 | 6/2005 | Leamon et al. |
| 2006/0003439 A1 * | 1/2006 | Ismagilov et al. ......... 435/287.2 |
| 2006/0037657 A1 | 2/2006 | Shibata et al. |
| 2007/0039866 A1 | 2/2007 | Schroeder |
| 2007/0068573 A1 | 3/2007 | Cox |
| 2007/0122314 A1 | 5/2007 | Strand et al. |
| 2007/0141593 A1 | 6/2007 | Lee |
| 2008/0023330 A1 | 1/2008 | Viovy |
| 2010/0209916 A1 | 8/2010 | Zon |

OTHER PUBLICATIONS

Curcio, Mario et al., "Continuous segmented-Flow Polymerase Chain Reaction for High-Throughput Miniaturized DNA Amplification", Analytical Chemistry, vol. 75(1), American Chemical Society, 1-7.

Hashimoto, et al., "On-line integration of PCR and cycle sequencing in capillaries: from human genomic DNA directly to called bases", *Nucleic Acids Research*, vol. 31, No. 8, 2003, 1-17.

Obeid, P. J. et al., "Microfabricated systems for nucleic acid analysis", *Critical Reviews in Clinical Laboratory Sciences*, CRC Press, Boca Raton, FL, vol. 41, No. 5-6, 429-465.

Auroux, Pierre-Alain et al., "Miniaturised nucleic acid analysis", *Lab on a Chip*, The Royal Society of Chemistry, vol. 4, 2004, 534-546.

Schneegass, et al., "Miniaturized flow-through PCR with different template types in a silicon chip thermocycler", *Lab on a Chip*; vol. 1, 2001, 42-49.

Waters, L. C. et al., "Microchip Device for Cell Lysis, Multiplex PCR Amplification, and Electrophoretic Sizing", *Analytical Chemistry*, vol. 70, No. 1, American Chemical Society, 1998, 158-162.

Burns, et al., "Microfabricated Structures for Integrated DNA Analysis", *Proc. Natl. Acad. Sci.*, vol. 93, May 1996, 5556-5561.

* cited by examiner

Resequencing using Sipper

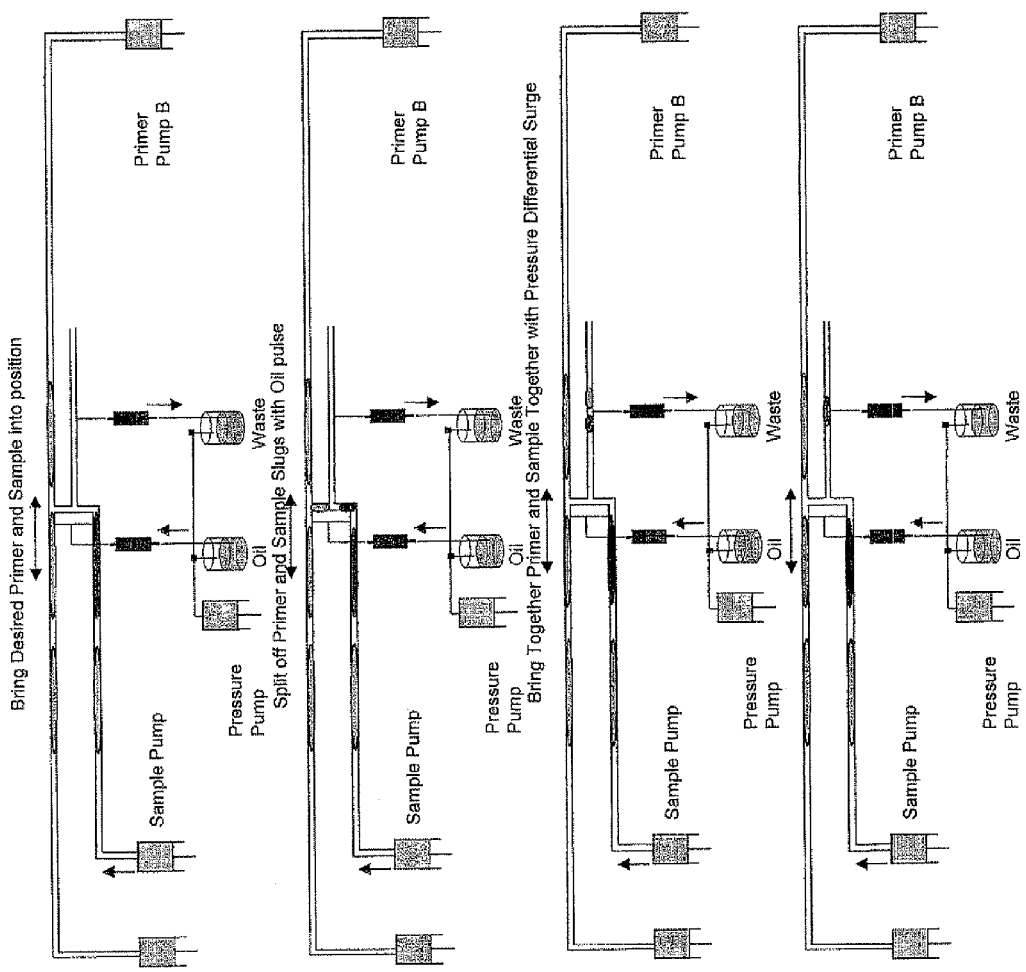

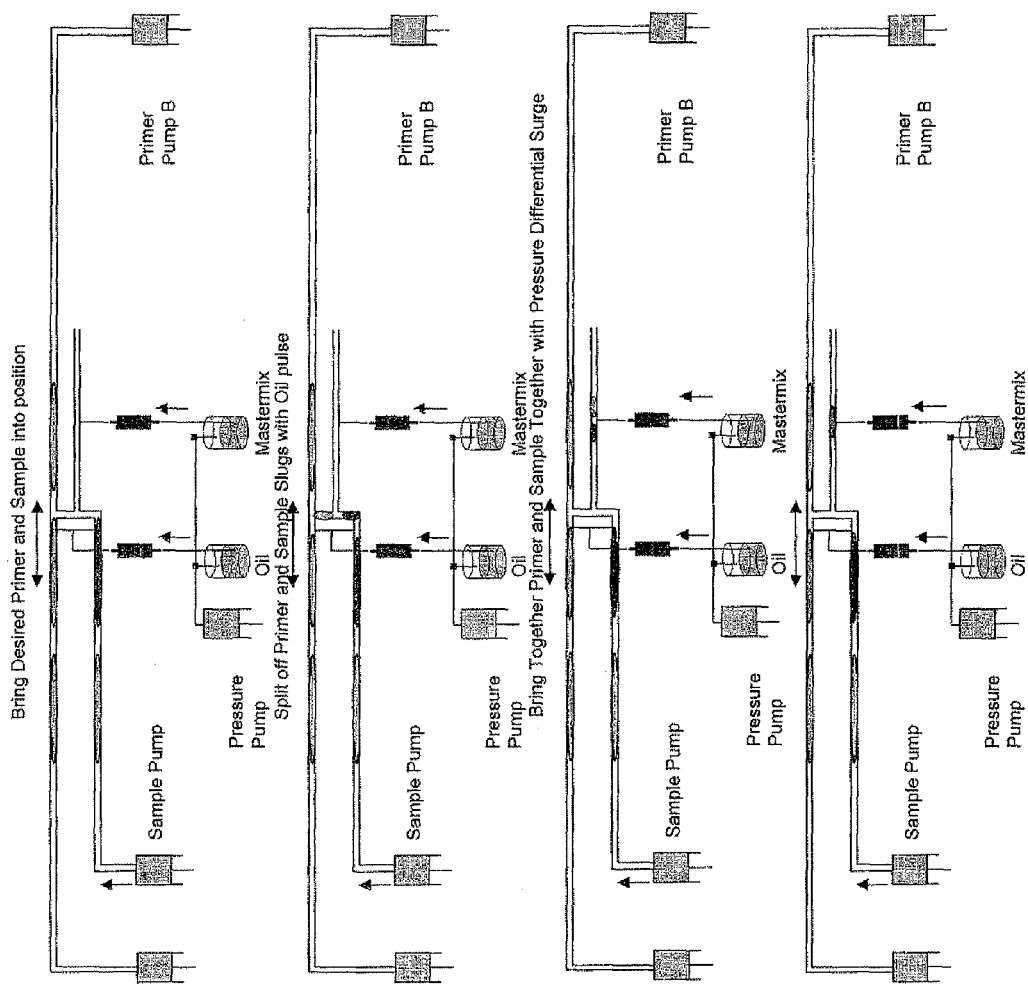

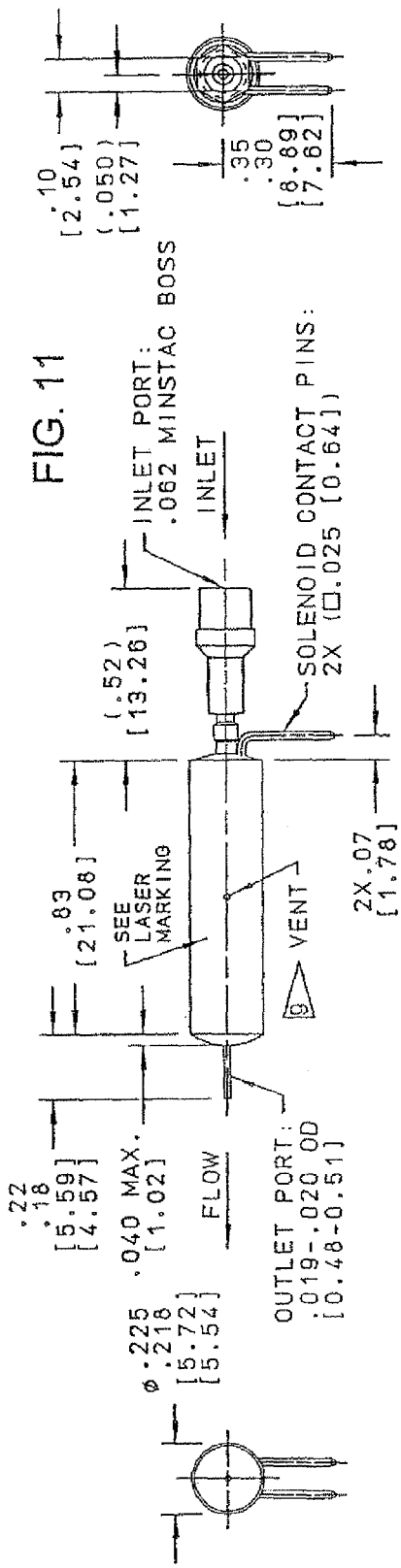

FIG. 12
Split/add for forward and reverse sequencing

*Step one: Uniform addition of oil splits discrete volumes (dv) in half, regardless of dv spacing. Relevant parameters are the two flow rates and the discrete volume size. Step two: Valves with pressurized reagents allows metered addition to alternate discrete volumes. Additions will be timed from detection of the first smaller dv in the split dv pair (say, 3a). Random spacing (of dvs 1, 2 and 3) will not affect volume of addition*

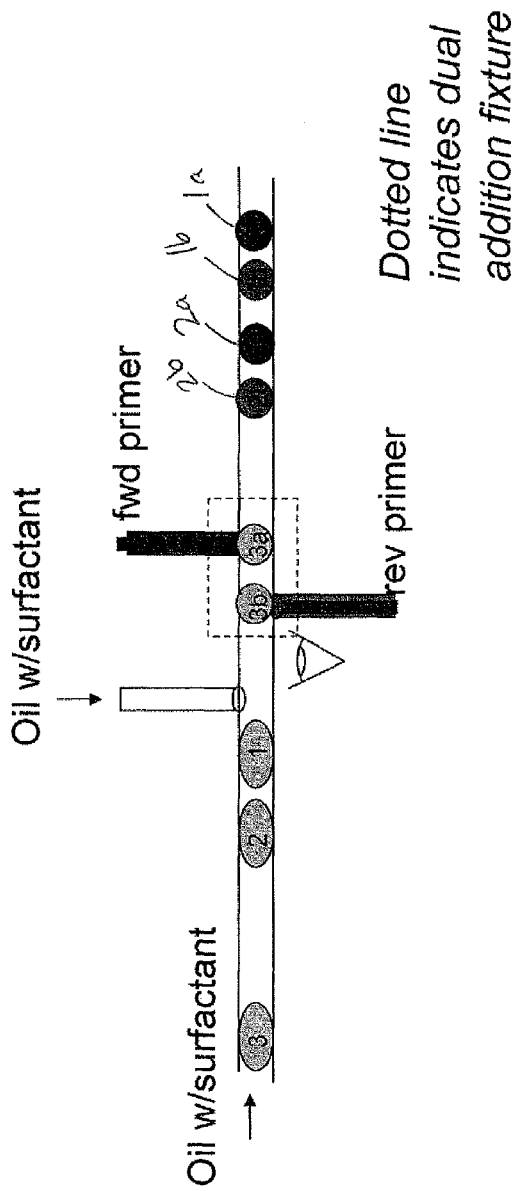

Discrete volume detection based on dye in oil

COMPOSITIONS, SYSTEMS, AND METHODS FOR IMMISCIBLE FLUID DISCRETE VOLUME MANIPULATION

CROSS REFERENCE TO RELATED APPLICATIONS

This application claims the benefit of priority under 35 U.S.C. §119(e) to U.S. Provisional Patent Application Nos. 60/891,225, and 60/891,208, which were filed on Feb. 22, 2007, and are explicitly incorporated in their entireties by reference herein.

FIELD

The present teachings relate to methods of fluid manipulation and systems and compositions for carrying out such methods.

BACKGROUND

Discrete volumes of a first fluid separated from one another by a second fluid that is immiscible with the first fluid, can sometimes undesirably coalesce with one another. Efforts to prevent such coalescence of discrete volumes can render the addition of a miscible fluid to the discrete volumes unfeasible. It would be desirable to prevent coalescence between two such adjacent immiscible fluid discrete volumes yet permit the addition of a third or addition fluid into one or both of the adjacent discrete volumes.

SUMMARY

According to various embodiments, a system is provided that comprises: a first conduit; a composition in the first conduit, the composition comprising an oil and discrete volumes of an aqueous fluid in the oil, the oil and the aqueous fluid being immiscible with one another and the discrete volumes being spaced apart from one another; a second conduit in fluid communication with the first conduit, at a junction; a valve disposed along the second conduit; and circuitry associated with the valve and configured to open the valve when one of the discrete volumes is present at the junction.

The pressurized addition of a miscible fluid (miscible with the first fluid) from the second conduit into a junction of the second conduit and the first conduit, where the composition described above is present in the first conduit, can result at least four outcomes, depending on the relative pressure difference (in order of increasing relative pressure): 1) the miscible addition fluid does not affect the passing discrete volume of first fluid, but forms a separate discrete volume of addition fluid either before or after the discrete volume of first fluid; 2) the miscible addition fluid splits the passing discrete volume into at least two smaller discrete volumes and forms a separate discrete volume of addition fluid between the first and second smaller discrete volumes of first fluid; 3) the miscible addition fluid coalesces with the discrete volume of first fluid forming a larger discrete volume of first and addition fluid; and 4) the miscible addition fluid breaks the discrete volume of first fluid into multiple small droplets, that do not coalesce. The boundaries of differential pressures between these outcomes are not fixed but can be affected by many variables, including at least the choice of spacing fluid and surfactant and the diameters of the first and second conduits.

The pressurized addition of the second fluid through the second conduit into a junction of the second conduit and the first conduit, where the composition described above is present in the first conduit, can result at least four outcomes, depending on the relative pressure difference (in order of increasing relative pressure): 1) the pressurized second fluid does not affect the passing discrete volume of first fluid, but increases the spacing between the discrete volume of first fluid and one of its adjacent discrete volumes in the composition; 2) the pressurized second fluid splits the passing discrete volume into at least two smaller discrete volumes spaced apart by second fluid; and 3) the pressurized second fluid breaks the discrete volume of first fluid into multiple small droplets, that do not coalesce.

In some embodiments, the valve can comprise a solenoid valve. The valve can be configured to rest in a closed position, and the valve can comprise a distal surface. The first conduit can have an inner surface and when the valve is in the closed position the distal surface of the valve can be flush with the inner surface of the first conduit. The system can further comprise a pump associated with the valve, and the circuitry is configured to actuate the valve and power the pump. The valve and pump combination can also be, for example, a metering pump, a piezo pump, a solenoid squeezing a tube acting a pump, and an ink jet pump.

According to various embodiments, a system is provided that comprises: a first conduit; a composition in the first conduit, the composition comprising an oil and discrete volumes of an aqueous fluid in the oil, the oil and the aqueous fluid being immiscible with one another and the discrete volumes being spaced apart from one another; a second conduit in fluid communication with the first conduit, at a junction; and a pump configured to pump a liquid through the second conduit and configured to provide one or more bursts of pressure within a 100 millisecond period. The pump can be configured to force liquid out of the second conduit and into the first conduit, at the junction, at a differentially higher pressure sufficient to disrupt the stability of the discrete volume's interface with the second fluid, allowing the forced liquid to coalesce with the discrete volume.

According to various embodiments, a system is provided that comprises: a first conduit; an oil in the first conduit; a second conduit in fluid communication with the first conduit, at a junction; an aqueous fluid in the second conduit, the oil and the aqueous fluid being immiscible with one another; a valve disposed along the second conduit; and a fluid movement system configured to open the valve and force portions of the aqueous fluid from the second conduit into the first conduit to form discrete volumes of the aqueous fluid spaced apart from one another, in the oil. In some embodiments, the first conduit can comprise a sidewall and the junction can comprise a hole through the sidewall.

According to various embodiments, a method is provided that comprises: flowing a composition of fluids through a first conduit, the composition of fluids comprising discrete volumes of a first fluid in a second fluid, the first fluid and the second fluid being immiscible with one another and the discrete volumes being spaced apart from one another by the first fluid; positioning a first discrete volume of the discrete volumes with a junction in the first conduit, the junction comprising a second conduit in fluid communication with the first conduit; and injecting an amount of an addition fluid from the second conduit into the junction at a differentially higher pressure so that the amount of addition fluid contacts and coalesces with the first discrete volume, the addition fluid being miscible with the first fluid but non-coalesceable with the first discrete volume if injected at a lower pressure. In some embodiments, the composition of fluids can comprise a surface active agent that is soluble in the first fluid and has a hydrophilic/lipophilic balance of from about 2 to about 5. The surface active agent can be present in the first fluid at a concentration of from about 0.1% by weight to about 10% by weight, based on the total weight of the first fluid and the surface active agent. The second fluid can comprise a polysiloxane and the first fluid can comprise an aqueous fluid. The surface active agent can comprise a polyalkyleneoxide-substituted siloxane. In some embodiments, the first fluid can comprise a polysiloxane and the surface active agent can comprise a polyalkyleneoxide-substituted polysiloxane. In some embodiments, the first fluid can comprise a non-fluorinated polysiloxane oil. In some embodiments, the first fluid can comprise a fluorinated oil.

According to various embodiments, a method is provided for forming discrete volumes of a first fluid in a second fluid wherein the first fluid and the second fluid are immiscible with one another and the discrete volumes are spaced apart from one another by the first fluid. The method can comprise: flowing the second fluid through a first conduit and to a junction of the first conduit with a second conduit, the junction comprising a fluid communication between the first conduit and the second conduit; opening a valve in the second conduit, the valve configured to assume an open position and a closed position and comprising a distal surface, wherein the first conduit has an inner sidewall and the distal surface is flush with the inner sidewall when the valve is in the closed position; and injecting an amount of first fluid from the second conduit and through the junction and into the first conduit, while the valve is in the open position, to form discrete volumes of the first fluid in the second fluid. The composition of fluids can comprise a surface active agent that is soluble in the second fluid and has a hydrophilic/lipophilic balance of from about 2 to about 5. The surface active agent can be present in the second fluid at a concentration of from about 0.1% by weight to about 10% by weight, based on the total weight of the first fluid and the surface active agent. In some embodiments, the second fluid can comprise polysiloxane and the first fluid can comprise an aqueous fluid.

According to various embodiments, a method of coalescing a discrete volume of an addition fluid with a discrete volume of a first fluid is provided. The method can comprise: flowing a composition of fluids through a first conduit, the composition of fluids comprising discrete volumes of a first fluid in a second fluid, and a discrete volume of an addition fluid, the first fluid and the second fluid being immiscible with one another, the addition fluid and the second fluid being immiscible with one another, the first fluid and the addition fluid being miscible with one another, and the discrete volume of the first fluid and the discrete volume of the addition fluid being spaced apart from one another by a portion of the second fluid; positioning the portion of the second fluid with a junction in the first conduit, the junction comprising a second conduit in fluid communication with the first conduit; and rapidly removing the portion of the second fluid at the junction to coalesce the discrete volume of the first fluid with the discrete volume of the addition fluid. In some embodiments, the discrete volume of addition fluid and the discrete volume of first fluid will not coalesce without the negatively pressurized removal of the second fluid due to the presence of a surface active agent in the second fluid.

BRIEF DESCRIPTION OF THE DRAWINGS

The skilled artisan will understand that the drawings described below are for illustrative purposes only. The drawings are not intended to limit the scope of the present teachings in any way.

FIGS. 9 and 10 are schematic diagrams of two respective processing systems according to various embodiments.

FIG. 11 is a technical drawing and specification sheet for an exemplary valve that can be used according to various embodiments.

FIG. 12 is a cross-sectional view of a system and method for carrying out a workflow according to various embodiments.

DESCRIPTION

Figure 1:
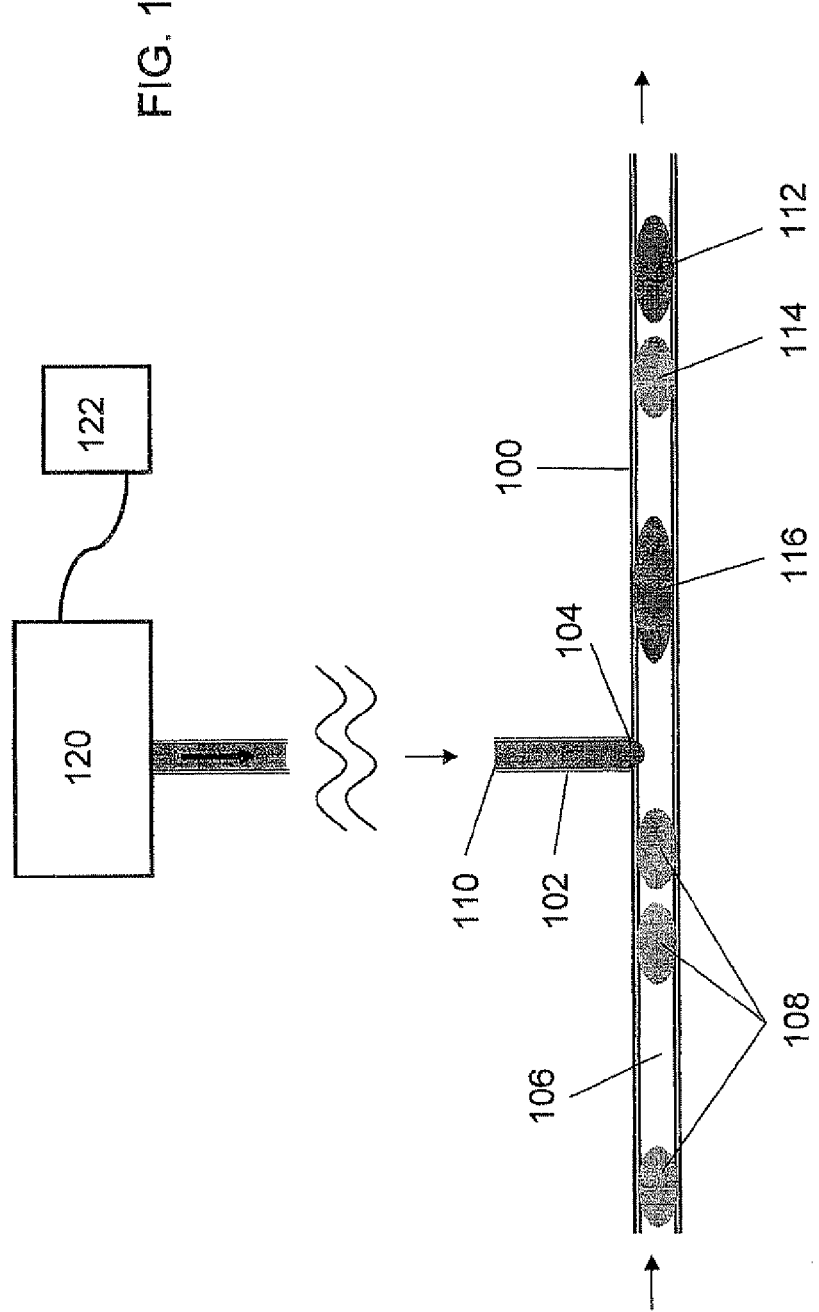
FIG. 1 is a cross-sectional view of a system and method for carrying out a workflow according to various embodiments.

According to various embodiments, a composition is provided that comprises an oil, for example, a non-fluorinated polyalkylpolysiloxane oil, discrete volumes of an aqueous fluid in the oil, and a surface active agent. The oil can comprise a silicone oil, for example, a non-fluorinated polyalkylpolysiloxane oil. The discrete volumes of aqueous fluid can be immiscible with one another and the discrete volumes can be spaced apart from one another with the oil in between. The composition can be provided in a conduit having an inner diameter that is about equal to a diameter of the discrete volumes of aqueous fluid, such that the discrete volumes can be arranged in a single file from within the conduit.

The surface active agent can be soluble in the oil and can have a hydrophilic/lipophilic balance (HLB) of from about 1.0 to about 8.0, from about 3.0 to about 6.0, for example, or from about 4.0 to about 5.0.

According to various embodiments, the surface active agent can be present in the non-fluorinated, polyalkylpolysiloxane oil at a concentration sufficient to prevent coalescence of the discrete volumes with one another for a period of 48 hours, when kept at a temperature in the range of about 0° C. to about 40° C. In some embodiments, the surface active agent can be present in the non-fluorinated, polyalkylpolysiloxane oil at a concentration sufficient to prevent coalescence of the discrete volumes with one another up to a temperature of at least 95° C. In some embodiments, the surface active agent can have an HLB and be present in the non-fluorinated, polysiloxane oil at a concentration that does not prevent coalescence of a discrete volume with a proximate body of addition fluid that is miscible with the first fluid of the discrete volume.

According to various embodiments, otherwise stable discrete volumes (those that do not coalesce when in close proximity to one another) can have their stability decreased through localized temperature increases and therefore coalesce. The localized temperature increase can be effectuated by resistive, microwave, inductive coupling, or acoustic energy, for example.

According to various embodiments, the oil can comprise a siloxane chain or ring according to the following structural formulas:

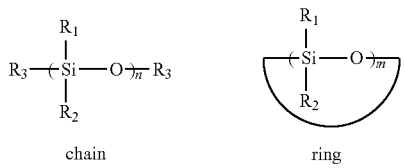

chain    ring where R1, R2 can each an alkyl, aryl, vinyl, or trifluoropropyl; R3 can be an alkyl, hydroxyl, or acetyl; and n is within the range of 2-40 and m is within the range of 3-6.

According to various embodiments, the oil can comprise a polysiloxane oil and the polysiloxane oil can comprise a di-, tri-, tetra-, or penta-, siloxane. In some embodiments, the polysiloxane oil can comprise a blend or mixture of two or more different oils. In some embodiments, the polysiloxane oil can comprise a blend or mixture of two or more polysiloxane oils. According to various embodiments, the polysiloxane oil can have a viscosity ranging from about 0.25 centistoke (cSt) to about 5.0 cSt, or from about 0.50 cSt to about 3.0 cSt, for example, from about 0.65 cSt to about 2.0 cSt.

According to various embodiments, the oil can comprise a polysiloxane oil and the polysiloxane oil can comprise a polydialkylcyclosiloxane or a blend of oils that comprises an polydialkylcyclosiloxane. According to various embodiments, the polydialkylcyclosiloxane can comprise a polydimethylcyclosiloxane. According to various embodiments, the polydimethylcyclosiloxane can comprise a decamethylcyclopentasiloxane.

According to various embodiments, the polysiloxane oil can comprise polyalkylpolysiloxane. According to various embodiments, the polyalkylpolysiloxane can comprise polymethyl-, propyl-, butyl-, pentyl-, hexyl-, octyl-, decyl-, polysiloxane. According to various embodiments, the dimethylpolysiloxane can comprise a methyl di-, tri-, tetra-, penta-, hexa-, octa-, deca-, siloxane.

In some embodiments, the composition can comprise a polyalkylpolysiloxane oil having a viscosity of from about 0.25 centistoke to about 3.0 centistokes at 25° C., for example, from about 0.5 centistoke to about 2.0 centistokes at 25° C. In some embodiments, for example, an oil can be used that also exhibits a viscosity in one or more of such ranges, at 90° C. The non-fluorinated, polyalkylpolysiloxane oil can, in some embodiments, comprise one or more of an alkyldisiloxane oil, an alkyltrisiloxane oil, and an alkyltetrasiloxane oil, and the alkyl groups can comprise methyl, ethyl, propyl, and the like, alkyl groups. In some embodiments, the oil can comprise a polydimethylpolysiloxane such as decamethyltetrasiloxane. In some embodiments, the oil can be non-fluorinated.

In some embodiments, the oil can comprise a mixture or blend of two or more oils, for example, a mixture of a polyalkylpolysiloxane oil and a polycyclosiloxane oil. An exemplary mixture comprises a ten to one weight ratio of decamethyltetrasiloxane to decamethylpentacyclosiloxane.

According to various embodiments, the surface active agent can be provided as a polydialkylsiloxane-polyalkyleneoxide at a concentration of from about 1.0% to about 20.0% by weight, dispersed in an alkylcyclosiloxane. According to various embodiments, the surface active agent can comprise about one percent by weight solution of alkylsiloxane-polyalkyleneoxide dispersed in a polysiloxane oil, which is then mixed with oil to form the first fluid described herein. In some embodiments, the surface active agent can comprise, for example, a detergent, a wetting agent, or an emulsifier.

According to various embodiments, the surface active agent can comprise a polyalkylene oxide. According to various embodiments, the polyalkylene oxide can comprise a polyethylene oxide (PEO) such as polyethylene glycol (PEG) or polypropylene glycol (PPG).

According to various embodiments, the surface active agent can comprise a backbone of polysiloxane, substituted with a polyalkylene oxide. According to various embodiments, the polysiloxane backbone can comprise a polyalkylsiloxane cross-linked with a polyalkylene oxide that can form a gel particle of average diameter ranging from about 1 micron to about 10 micron. According to various embodiments, the average diameter of the gel particle is about 5 microns.

According to various embodiments, the surface active agent can comprise a polyalkyleneoxide-substituted siloxane, for example, a polyethylene glycol-substituted siloxane. An exemplary surface active agent is DC 9011 surfactant from Dow Corning. The surface active agent can be dispersed in a carrier oil before it is mixed with the oil described herein. For example, the surface active agent can be dispersed in a polysiloxane oil or in a polycyclosiloxane oil, before it is mixed with a polyalkylpolysiloxane oil. In an exemplary embodiment, the surface active agent can comprise a polyalkyleneoxide-substituted polysiloxane dispersed in a cyclic polysiloxane oil, for example, in D5, a decamethylpentacyclosiloxane oil.

According to various embodiments, the surface active agent can comprise a silicone polyether, for example, PEG/PPG-18 dimethicone (10% by weight) in cyclopentasiloxane. An exemplary surfactant of this type is SILSURF 400 R available from Siltech Corporation of Toronto, Ontario, Canada. Like other surface active agents, SILSURF 400R can be provided as a dispersion in a carrier oil, such as a polycyclosiloxane oil or decamethylpentacyclosiloxane, for example, in a 10% by weight dispersion, based on the total weight of the dispersion. The carrier oil can be miscible with the oil used as the second fluid, and can make up from about 1% to about 30% by weight of the total weight of the oil, carrier oil, and surface active agent, combined, for example, 10% by weight of such total weight.

Another exemplary surface active agent that can be used is GRANSURF 77 available from Grant Industries, Elmwood Park, N.J.. GRANSURF 77 comprises PEG-10 dimethicone and can be provided neat or in a dispersion, for example, in a dispersion comprising a polycyclosiloxane oil.

The surface active agent can be provided in any suitable concentration in an oil or oil mixture. Exemplary concentrations can include, for example, about 0.1 to about 10% by weight surface active agent based on the total weight of the combined surface active agent and oil or oil blend. Concentrations of from about 0.25% by weight to about 5.0% by weight can be used, as can concentrations of from about 0.5% by weight to about 3.0% by weight, for example, about 1.0% by weight surface active agent.

According to various embodiments, the oil can comprise a fluorinated oil and the surface active agent can comprise a compound soluble in the fluorinated oil at a concentration sufficient to prevent discrete volumes of aqueous fluid therein from coalescing when in close proximity with each other, or in other words, "touching".

According to various embodiments, a system is provided that comprises: a first conduit; a composition in the first conduit, the composition comprising an oil and discrete volumes of an aqueous fluid in the oil, the oil and the aqueous fluid being immiscible with one another and the discrete volumes being spaced apart from one another; a second conduit in fluid communication with the first conduit, at a junction; a valve disposed along the second conduit; and circuitry associated with the valve and configured to open the valve when one of the discrete volumes is present at the junction.

In some embodiments, the valve can comprise a solenoid valve. The valve can be configured to rest in a closed position, and the valve can comprise a distal surface. The first conduit can have an inner surface and when the valve is in the closed position the distal surface of the valve can be flush with the inner surface of the first conduit. The system can further comprise a pump associated with the valve, and the circuitry is configured to actuate the valve and power the pump. In some embodiments, the circuitry can be programmed to actuate the valve, from a non-actuated position, one or more times within a 100 millisecond period, upon a triggering event. The triggering event comprises a detection of one of the discrete volumes at or near the junction. The circuitry can be programmed to actuate the valve for a period of from about 0.1 millisecond to about 10 milliseconds, one or more times within a 100 millisecond period. In some embodiments, the valve can comprise an outlet port and the pump is configured to force a liquid through the outlet port at a differentially higher pressure of from about three psi to about 25 psi. In some embodiments, the first conduit has an inner diameter of from about 0.010 to about 0.10 inch, the valve comprises an outlet port, and the outlet port has inner diameter of from about 0.010 to about 0.10 inch.

According to various embodiments, a system is provided that comprises: a first conduit; a composition in the first conduit, the composition comprising an oil and discrete volumes of an aqueous fluid in the oil, the oil and the aqueous fluid being immiscible with one another and the discrete volumes being spaced apart from one another; a second conduit in fluid communication with the first conduit, at a junction; and a pump configured to pump a liquid through the second conduit and configured to provide multiple bursts of pressure within a 100 millisecond period. The pump can be configured to force liquid out of the second conduit and into the first conduit, at the junction, at a differentially higher pressure of from about three psi to about 25 psi, for example, at a pressure of from about three psi to about seven psi. The valve and pump combination can also be, for example, a metering pump, a piezo pump, a solenoid squeezing a tube acting a pump, and an ink jet pump.

According to various embodiments, a system is provided that comprises: a first conduit; an oil in the first conduit; a second conduit in fluid communication with the first conduit, at a junction; an aqueous fluid in the second conduit, the oil and the aqueous fluid being immiscible with one another; a valve disposed along the second conduit; and a fluid movement system configured to open the valve and force portions of the aqueous fluid from the second conduit into the first conduit to form discrete volumes of the aqueous fluid spaced apart from one another, in the oil. In some embodiments, the first conduit can comprise a sidewall and the junction can comprise a hole through the sidewall. The fluid movement system can comprise one or more pumps and at least one of the one or more pumps can be configured to pump the aqueous fluid through the second conduit at a predetermined rate. The valve can be configured to be actuated for a period of time based on the rate that the discrete volumes flow to provide discrete volumes of a pre-selected volume. The valve can be opened for a timer period depending on the input pressure, resistance to flow, and the desired volume. The interval between valve openings then is the rate at which discrete volumes are created. In some embodiments, the first conduit can have an inner surface, the valve can comprise a distal surface, and the distal surface of the valve can be flush with the inner surface of the first conduit.

According to various embodiments, the circuitry can be programmed to actuate the valve, from a non-actuated position, one or more times within a 100 millisecond period. In some embodiments, the rate of actuation can be slower and system throughput will be reduced as a result. In some embodiments, the circuitry can be programmed to actuate the valve for a period of from about 0.1 millisecond to about 10 milliseconds, one or more times within a 100 millisecond period. In some embodiments, the first conduit can have an inner diameter of from about 0.010 to about 0.10 inch, the valve can comprise an outlet port, and the outlet port can have an inner diameter of from about 0.010 to about 0.10 inch.

According to various embodiments, a method is provided that comprises: flowing a composition of fluids through a first conduit, the composition of fluids comprising a first fluid and discrete volumes of a second fluid in the first fluid, the first fluid and the second fluid being immiscible with one another and the discrete volumes being spaced apart from one another by the first fluid; positioning a first discrete volume of the discrete volumes with a junction in the first conduit, the junction comprising a second conduit in fluid communication with the first conduit; and injecting an amount of an addition fluid from the second conduit into the junction at a sufficiently differentially higher pressure so that the amount of addition fluid contacts and coalesces with the first discrete volume, the addition fluid being miscible with the second fluid but non-coalesceable with the first discrete volume if injected at a lower pressure. In some embodiments, the composition of fluids can comprise a surface active agent that is soluble in the first fluid and has a hydrophilic/lipophilic balance of from about 2 to about 5. The surface active agent can be present in the first fluid at a concentration of from about 0.1% by weight to about 10% by weight, based on the total weight of the first fluid and the surface active agent. The first fluid can comprise polysiloxane and the second fluid can comprise an aqueous fluid. The surface active agent can comprise a polyalkyleneoxide-substituted siloxane. In some embodiments, the first fluid can comprise a polysiloxane and the surface active agent can comprise a polyalkyleneoxide-substituted polysiloxane.

In some embodiments, the second fluid can comprise an oil, the first fluid can comprise an aqueous fluid, and the surface active agent exhibits a hydrophilic/lipophilic balance of from about 2 to about 5. The addition fluid can be injected from the second conduit into the junction at a pressure of about five psi or greater. The injecting can comprise opening a valve disposed in the second conduit. In some embodiments, the injecting can comprise generating single or multiple bursts of pressure within a 100 millisecond period. The injecting can comprise generating one or more bursts of pressure of at least about five psi each, within a 100 millisecond period.

In some embodiments the flowing a composition of fluids can comprise pushing the composition of fluids through the first conduit. In some embodiments, the flowing a composition of fluids can comprise pulling the composition of fluids through the first conduit.

According to various embodiments, a method is provided for forming discrete volumes of a first fluid in a second fluid wherein the first fluid and the second fluid are immiscible with one another and the discrete volumes are spaced apart from one another by the first fluid. The method can comprise: flowing the second fluid through a first conduit and to a junction of the first conduit with a second conduit, the junction comprising a fluid communication between the first conduit and the second conduit; opening a valve in the second conduit, the valve configured to assume an open position and a closed position and comprising a distal surface, wherein the first conduit has an inner sidewall and the distal surface is flush with the inner sidewall when the valve is in the closed position; and injecting an amount of first fluid from the second conduit and through the junction and into the first conduit, while the valve is in the open position, to form discrete volumes of the first fluid in the second fluid. The composition of fluids can comprise a surface active agent that is soluble in the second fluid and has a hydrophilic/lipophilic balance of from about 2 to about 5. The surface active agent can be present in the second fluid at a concentration of from about 0.1% by weight to about 10% by weight, based on the total weight of the second fluid and the surface active agent. In some embodiments, the second fluid can comprise polysiloxane and the first fluid can comprise an aqueous fluid.

In some embodiments, the second fluid can be injected from the second conduit into the junction at a pressure of about five psi or greater. The injecting can comprise opening a valve disposed in the second conduit. The injecting can comprise generating single or multiple bursts of pressure within a 100 millisecond period. The injecting can comprise generating one or more bursts of pressure of at least about five psi each, within a 100 millisecond period.

According to various embodiments, a method of coalescing a discrete volume of an addition fluid with a discrete volume of a second fluid, is provided. The method can comprise: flowing a composition of fluids through a first conduit, the composition of fluids comprising discrete volumes of a first fluid in a second fluid, and a discrete volume of an addition fluid, the first fluid and the second fluid being immiscible with one another, the addition fluid and the second fluid being immiscible with one another, the first fluid and the addition fluid being miscible with one another, and the discrete volume of the first fluid and the discrete volume of the addition fluid being spaced apart from one another by a portion of the first fluid; positioning the portion of the second fluid in a junction in the first conduit, the junction comprising a second conduit in fluid communication with the first conduit; and removing the portion of the second fluid at the junction to coalesce the discrete volume of the first fluid with the discrete volume of the addition fluid.

According to various embodiments, the present teachings relate to systems and methods of manipulating a composition that comprises an oil, for example, a non-fluorinated polyalkylpolysiloxane oil, discrete volumes of an aqueous fluid in the oil, and a surface active agent. The oil can comprise a silicone oil, for example, a non-fluorinated polyalkylpolysiloxane oil. The discrete volumes of aqueous fluid can be immiscible with one another and the discrete volumes can be spaced apart from one another with the oil in between. In some embodiments, the composition can be provided in a conduit having an inner diameter that is about equal to a diameter of the discrete volumes of aqueous fluid, such that the discrete volumes can be arranged in a single file form within the conduit.

Referring now to the drawings and as shown in FIG. 1, the system exemplified can comprise a first conduit 100 in fluid communication with a second conduit 102 at a junction 104. A composition comprising a non-fluorinated polyalkylpolysiloxane oil 106 and discrete volumes of aqueous fluid 108 travels through first conduit 100 in the indicated direction. The non-fluorinated polyalkylpolysiloxane oil 106 and the aqueous fluid 108 are immiscible with one another and the discrete volumes of aqueous fluid 108 are spaced apart from one another. An addition fluid 110 in second conduit 102 can be added to a discrete volume of aqueous fluid 108 at the junction 104. According to various embodiments, a constant stream of addition fluid 110 can be dispensed through the second conduit 102. According to various embodiments, the addition fluid 110 can be dispensed intermittently, periodically, or on demand, through the second conduit 102. The volume flow of addition fluid 110 can be controlled so as to dispense a desired volume of addition fluid 110 at the junction 104 per unit of time.

The system can further comprise a pump 120 and a control apparatus 122 configured to provide the addition fluid 110 to the discrete volumes of aqueous fluid 108. Pump 120 and apparatus 122 can control the flow rate of addition fluid 110 so that a desired amount of addition fluid can be added to each discrete volume of aqueous fluid 108 at junction 104. Pump 120 and control unit 122 can be configured to pump addition fluid 110 continuously into junction 104, intermittently into junction 104, periodically into junction 104, or on demand into junction 104. In some embodiments, pump 120 and control unit 122 can be configured to pump addition fluid 110 continuously, at a low pressure, low flow rate punctuated by pulses of high pressure. In some embodiments, a pump and control unit can similarly be used to control the flow of non-fluorinated polyalkylpolysiloxane oil 106 and discrete volumes of aqueous fluid 108 traveling through first conduit 100 by pushing the composition in the direction indicated. In some embodiments, a pump and control unit can similarly be used to control the flow of non-fluorinated polyalkylpolysiloxane oil 106 and discrete volumes of aqueous fluid 108 traveling through first conduit 100 by pulling the composition in the direction indicated.

In some embodiments, the discrete volumes of aqueous fluid 108 traveling through first conduit 100 may be unevenly spaced in the polyalkylpolysiloxane oil 106. Consequently, the discrete volumes of aqueous fluid 108 can potentially receive unintended amounts of addition fluid 110 if the flow of addition fluid 110 was to be continuous, and at a constant rate. For example, while some discrete volumes of aqueous fluid 112 may receive the intended amount of addition fluid 110, other discrete volumes such as 114 may receive less than the intended amount of fluid, and other discrete volumes such as 116 may receive more than the intended amount of addition fluid.

Figure 2:
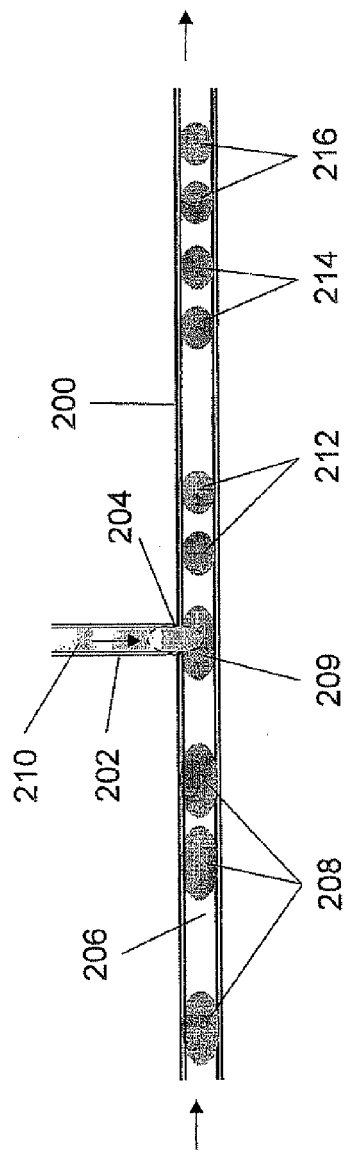
FIG. 2 is a cross-sectional view of a system and method for carrying out a workflow according to various embodiments.

In the embodiment shown in FIG. 2, a first conduit 200 and a second conduit 202 are in fluid communication with each other at a junction 204. A composition comprising a non-fluorinated polyalkylpolysiloxane oil 206 and discrete volumes of aqueous fluid 208 travels through the first conduit 200 in the direction indicated. As a discrete volume of aqueous fluid 209 reaches junction 204, a volume of non-fluorinated polyalkylpolysiloxane oil 210 can be injected into the composition through the second conduit 202. In various embodiments, the oil 210 can be injected with a quick pulse or burst of sufficient pressure such that the discrete volume of aqueous fluid 209 can be split into at least two discrete volumes of aqueous fluid 212. In various embodiments, the non-fluorinated polyalkylpolysiloxane oil 210 can be continuously flowed through conduit 202 at a constant velocity into junction 204. In various embodiments, the flowrate of the non-fluorinated polyalkylpolysiloxane oil 210 is sufficient to split the discrete volume of aqueous fluid 209 into at least two discrete volumes of aqueous fluid 212 as it passes through junction 204. A result of continuously flowing the oil 210 into junction 204 is that the spacing between discrete volumes of aqueous fluid is increased. In various embodiments, the discrete volumes 212 comprise a pair of nearly identical discrete volumes. The split discrete volumes of aqueous fluid 212, 214, and 216 can remain non-coalesced as they continue to travel through the first conduit 200.

In the embodiment shown in FIG. 2, a pump 220 and control apparatus 222 can apply a positive pressure to second conduit 202 causing the addition of oil 210 through the second conduit 202. All pressures are relative, for example, a partial vacuum could be placed on the output of conduit 200.

Figure 3:
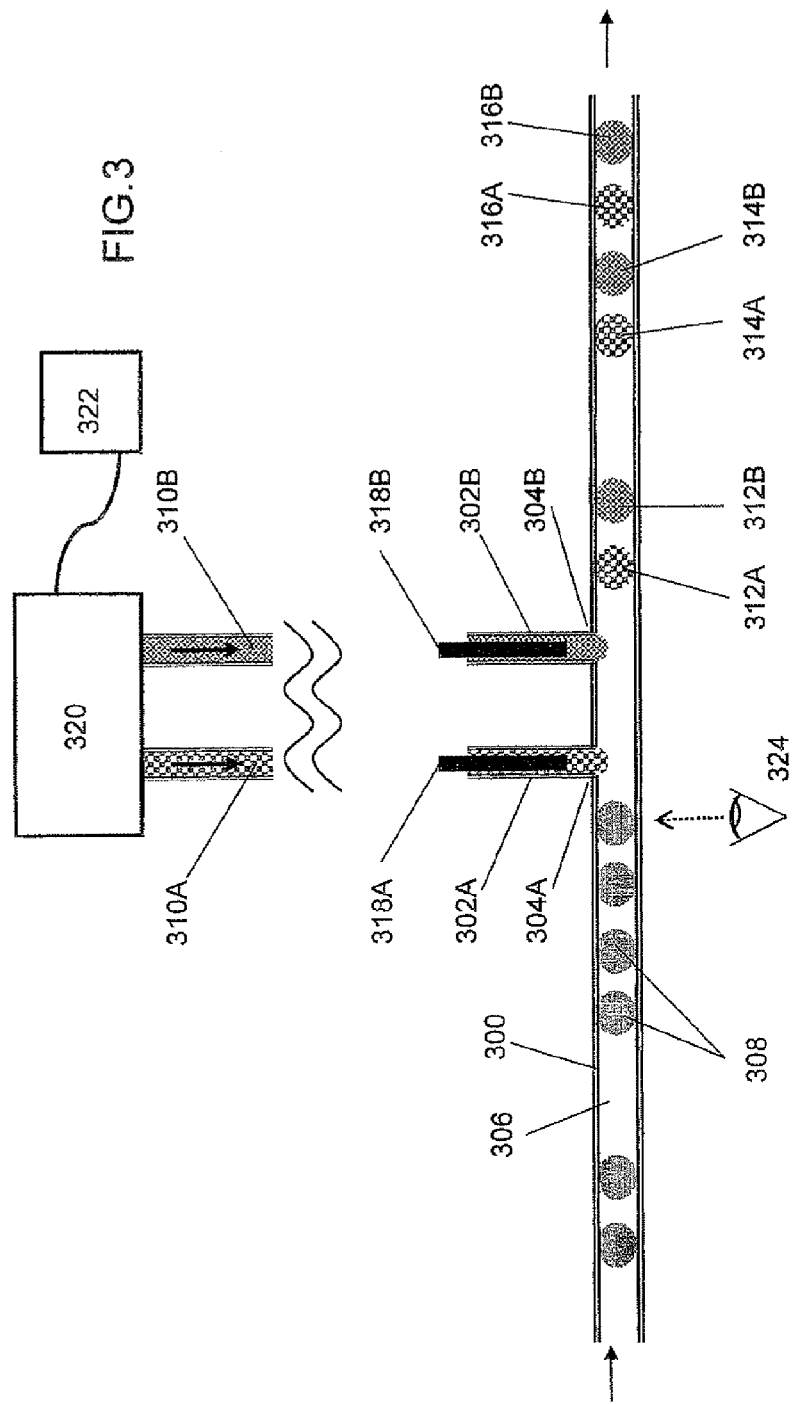
FIG. 3 is a cross-sectional view of a system and method for carrying out a metered workflow according to various embodiments.

In the embodiment shown in FIG. 3, a system is provided that comprises a first conduit 300 and at least a pair of second conduits 302A and 30213 both in fluid communication with the first conduit 300 at a junction 304A or 304B. A composition comprising a non-fluorinated polyalkylpolysiloxane oil 306 and discrete volumes of an aqueous fluid 308 travels through the first conduit 300 in the indicated direction. As a discrete volume of aqueous fluid 308 travels through the first conduit 300 and past a junction 304A and/or 30413, an addition fluid 310A and/or 310B can be injected into the discrete volume 308, through the second conduit 302A and/or 302B. The discrete volumes of aqueous fluid 312A and 312B, 314A and 314B, and 316A and 316B, comprising the addition fluid 310A and/or 310B, remain non-coalesced as they continue to travel through the first conduit 300.

According to various embodiments, as shown in FIG. 3, the system can comprise at least one valve 318A and 318B associated with second conduits 302A and/or 302B and configured to control the amount of addition fluid 310A and/or 310B flowing through second conduits 302A and/or 302B. The valve 318A and/or 318B can be, for example, a solenoid valve. The solenoid valve can be, for example, a high-speed, two-way solenoid valve such as VHS SP INKX 0514950A available from Lee Company, Essex, Conn. The valves can be controlled by a valve control apparatus such as, for example, a waveform generator. The wave form generator can be, for example, an Agilent waveform generator, model number 33220A from Agilent Technologies, Inc., Santa Clara, Calif. In some embodiments, the solenoid valve can be controlled by a system controller.

According to the embodiment shown in FIG. 3, addition fluid 310A can be added, for example, to discrete volumes of aqueous fluid 308 at the junction 304A, producing discrete volumes of aqueous fluid 312A, 314A, and 316A. The addition fluid 310B can be added, for example, to discrete volumes of aqueous fluid 308 at junction 304B, producing discrete volumes of aqueous fluid 312B, 314B and 316B. According to various embodiments shown in FIG. 3, both addition fluids 310A and 310B can be added to a single discrete volume of aqueous fluid 308. According to various embodiments, multiple second conduits 302, each with an addition fluid 310, can be in fluid communication with the first conduit 300.

According to various embodiments, as shown in FIG. 3, the system can comprise a sensor 324 for monitoring the composition in the first conduit 300. Greater details about such sensors and their components can be found, for example, in U.S. patent application Ser. No. 11/508,756, filed on Aug. 22, 2006, which is incorporated herein in its entirety by reference. The sensor 324 can detect and monitor, for example, the discrete volumes of aqueous fluid 308 traveling through the first conduit 300. In various embodiments, sensor 324 may detect a fluorescent dye in aqueous fluid 308.

The sensor 324 can be in communication with a pump 320 and a control apparatus 322 to provide a metered addition of addition fluid 310A and/or 310B to the discrete volumes of aqueous fluid 308. In some embodiments, there can be a pump for each valve. In some embodiments, there can be one pump for all valves. All possible combinations of number of valves associated with number of pumps in between these two extremes can be incorporated. In the embodiment shown in FIG. 3, the selection and addition of addition fluid 310A and/or 310B can be keyed off the detection of a discrete volume of aqueous fluid 308. Accordingly, any random spacing existing between the discrete volumes of aqueous fluid 308 will not affect the volume of addition fluid 310A and/or 310B, and the additions to the discrete volumes 308 can be uniform and very precise. In the embodiment shown in FIG. 3, the discrete volumes of aqueous fluid with the added addition fluid 310A and/or 310B, indicated as 312A, 312B, 314A, 314B, 316A and 31613, remain non-coalesced as they continue to travel through the first conduit 300.

In one embodiment of the system represented in FIG. 3, the addition fluid 310A and/or 310B can be, for example, different sequencing primers such as reverse and/or forward sequencing primers. An embodiment could comprise, for example, the system shown in FIG. 2 whereby the discrete volume of aqueous fluid 208 is split in half to form a pair of discrete volumes of aqueous fluid 212. The pairs of discrete volumes of aqueous fluid 212, 214, and 216 then continue to travel through the first conduit, feeding into the system shown into FIG. 3. The pairs of discrete volumes of aqueous fluid, now shown as 308 in FIG. 3, travel through the first conduit 300 where reverse primer 310A or forward primer 310B can then be added to alternate discrete volumes of aqueous fluid 312A and 3128 of the pair of discrete volumes 308. The addition of forward and reverse primers can be performed sequentially or simultaneously. In some embodiments, including those for use in sequence detection applications, a larger number of junctions and reagents can be incorporated in the system of FIG. 2.

Figure 4:
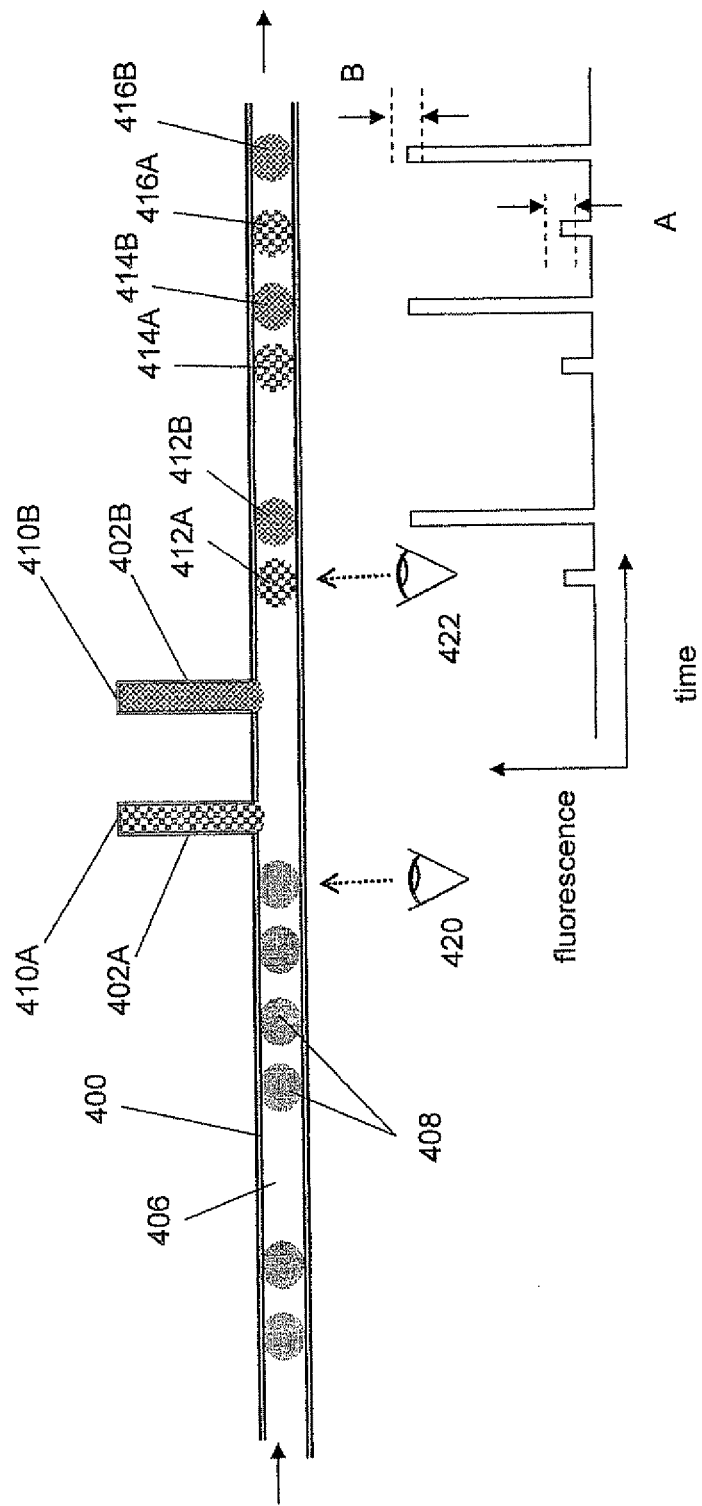
FIG. 4 is a cross-sectional view of a system for carrying out a metered workflow according to various embodiments.

As shown in FIG. 4, the system can further comprise a method for tracking the discrete volumes of aqueous fluid 412-416 as they travel through the conduit 400. The system can comprise the addition of spectrally resolvable dyes to the discrete volumes. The dyes can be added, for example, by including them in the addition fluid 410A and/or 4108. A dye detection sensor 422 can be used to detect the added dye as the discrete volumes 412-416 pass through the conduit 400. The dyes can be, for example, at least two different spectrally resolvable dyes emitting at different wavelengths, or they can be, for example, two different concentrations of the same dye. In various embodiments, the dye(s) may be the same or different from the dye that may be already present in discrete volumes of aqueous fluid 308. In some embodiments, SYBR green can be added to the discrete volumes prior to PCR, and can be detected using a blue light, for example, a blue LED detection sensor (e.g., labeled SlugOmeter in FIGS. 6-8) to trigger the addition of addition fluid and two concentrations of a "red" dye can be used to distinguish the forward and reverse reactions.

In the embodiment shown in FIG. 4, addition fluids 410A and 410B each contain a different concentration of the same fluorescent dye. Accordingly, each discrete volume of aqueous fluids of the pair of discrete volumes of aqueous fluid 412A, 412B, 414A, 414B, and 416A, 416B is identified and tracked by one of the two different concentrations of fluorescent dye. The different concentrations of the same dye can provide resolvable threshold values for identifying the contents of each individual discrete volume. In the system shown in FIG. 4, forward and reverse sequencing primers, for example, can be added with spectrally resolvable dye in the addition fluid 410A and 410B. Accordingly, the discrete volumes of aqueous fluid 412-416, comprising forward or reverse sequencing reaction mixtures, can be identified and monitored throughout the system.

Figure 5:
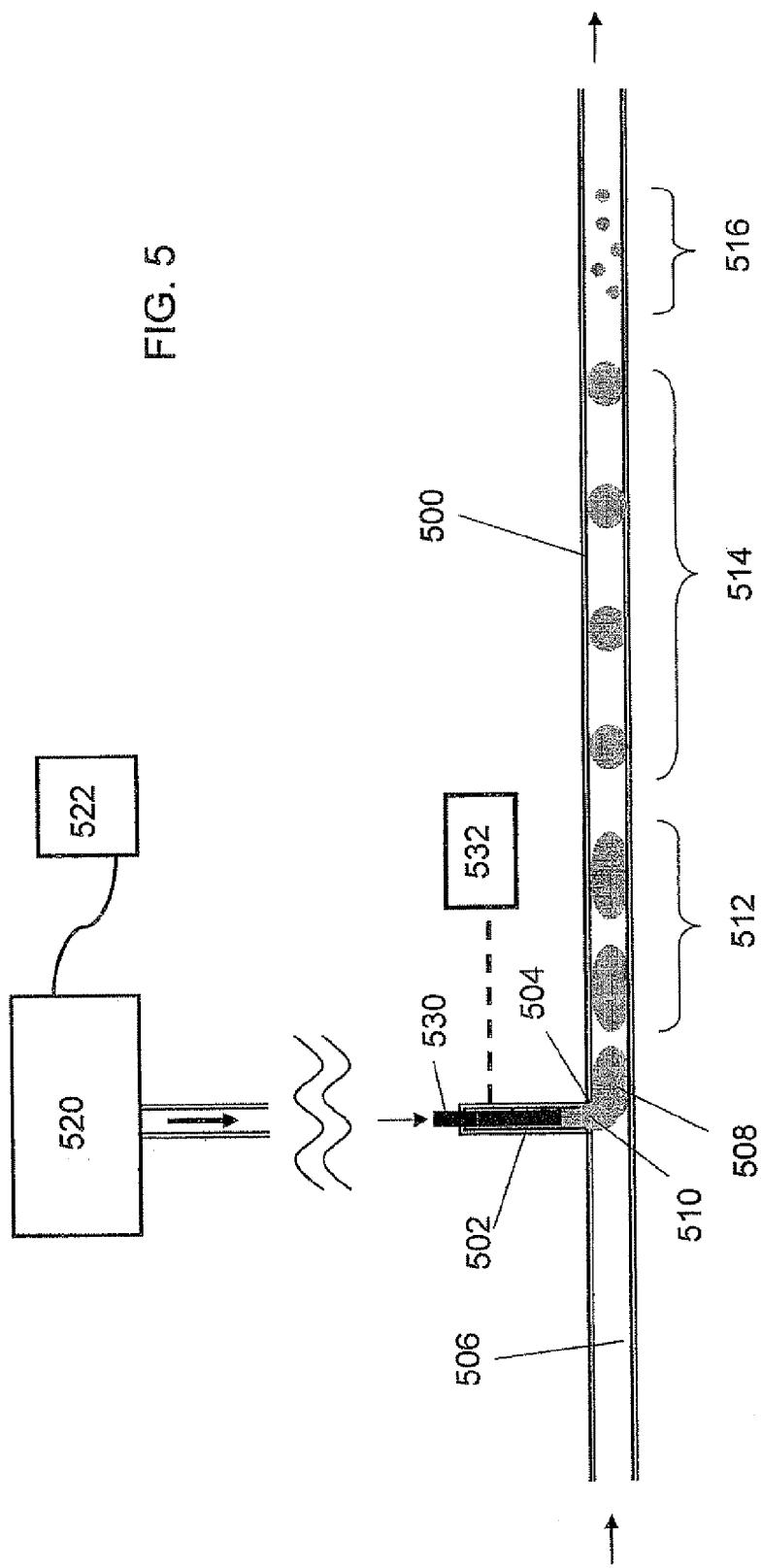
FIG. 5 is a cross-sectional view of a system and method for carrying out a variable metered workflow according to various embodiments.

In the embodiment found in FIG. 5, a system is provided that comprises a first conduit 500 and a second conduit 502 in fluid communication with the first conduit 500 at a junction 504. A composition comprising a non-fluorinated polyalkylpolysiloxane oil 506 and discrete volumes of an aqueous fluid 508, 512, 514, and 516, travels through first conduit 500 in the indicated direction. A pump 520 and a control apparatus 522 are configured to provide the aqueous fluid 510 through the second conduit 502. A valve 530 and a valve control apparatus 532 are configured to control the amount of aqueous fluid 510 in the discrete volume 508, and to control the spacing between adjacent discrete volumes. The valve 530 can be, for example, a solenoid valve. The solenoid valve can be, for example, a high-speed, two-way solenoid valve such as VHS SP INKX 0514950A available from Lee Company, Essex, Conn. The valve control apparatus 532 can be, for example, a waveform generator. The waveform generator can be, for example, an Agilent waveform generator, model number 33220A from Agilent Technologies, Inc., Santa Clara, Calif. The valve control apparatus 532 can be a system controller.

In the embodiment shown in FIG. 5, the volume of the discrete volume of aqueous fluid 512, 514, and 516, and the spacing of the discrete volumes of aqueous fluid 512, 514, and 516 can be controlled by varying the length of time and the intervals in which the valve 530 is open. Further control of the volume and spacing can be controlled by varying the pressure of the aqueous fluid 510 in the second conduit 502 and/or by varying the flow rate of the oil 506 and resistance to flow in the second conduit 502. The resistance to flow can be controlled by the size of the orifice of the junction, or can be an orifice elsewhere, or can be provided by the resistance to flow by a length of tubing. For example, the aqueous fluid 510 can be pressurized with pump 520 and pump control apparatus 522. According to various embodiments, the fluid can be pressurized at a range of about 1 to 50 PSI, or at a range of about 1 to 10 PSI, for example, about 5 PSI. According to various embodiments, the valve 530 can be set to remain open for a range of about 0.1 to 10 ms, for example, 1 ms. According to various embodiments, the valve 530 can be set to cycle about 1 to 100 times within 100 ms, for example, 10 cycles. According to various embodiments, the flow rate of polyalkylpolysiloxane oil 506 can be controlled to flow at a rate of about 0.01 to 100 uL/s, for example, about 0.75 uL/s. In some embodiments, multiple fluid additions can be made to a single discrete volume from one addition port.

As shown in FIG. 5, the volume and spacing of the discrete volumes of aqueous fluid 512-516 can be controlled by varying the parameters of pressure, oil flow rate, and pulse rate while keeping the junction 504 size constant. According to the embodiment shown in FIG. 5, the discrete volume size and spacing can be controlled to produce discrete volumes of aqueous fluid 512, 514, and 516. The discrete volumes of aqueous fluid 512-516 can remain non-coalesced as they continue to travel through the first conduit 500. According to the embodiment shown in FIG. 5, by controlling the parameters of pressure, oil flow rate, and pulse rate, pulse duration, and flow resistance, the discrete volume size and spacing can be reproduced from instrument to instrument.

Figure 6:
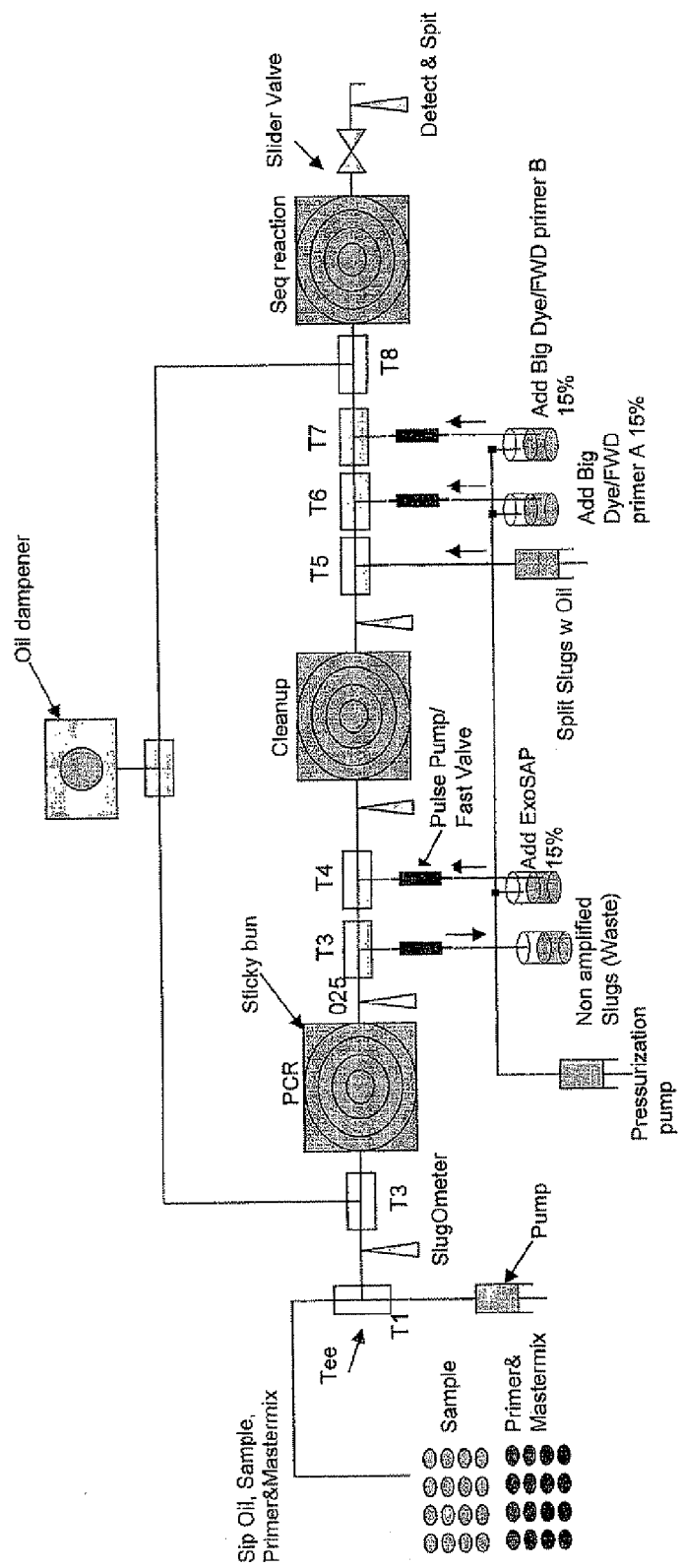
FIGS. 6-8 are schematic diagrams of three respective processing systems according to various embodiments.
Figure 7:
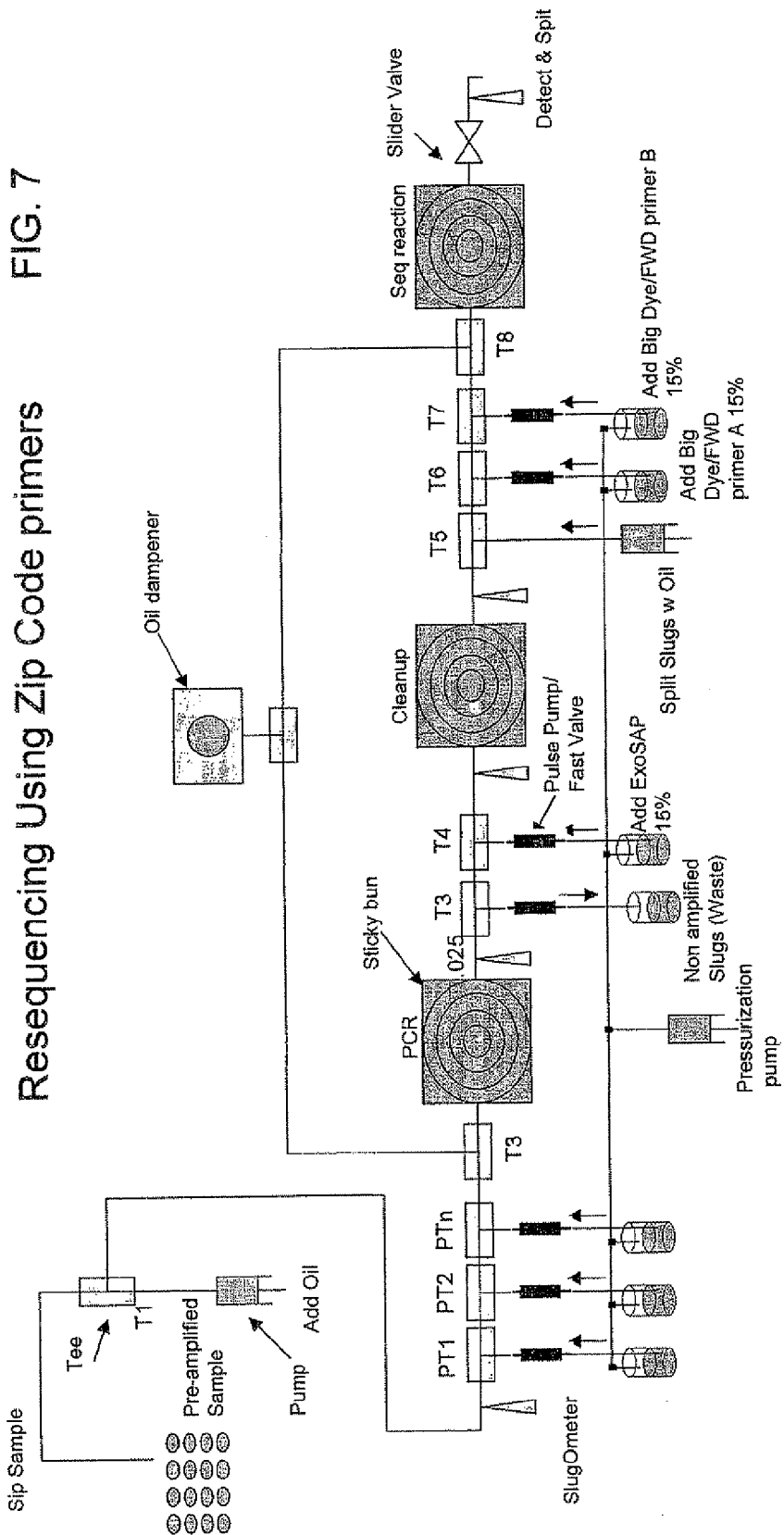
Figure 8:
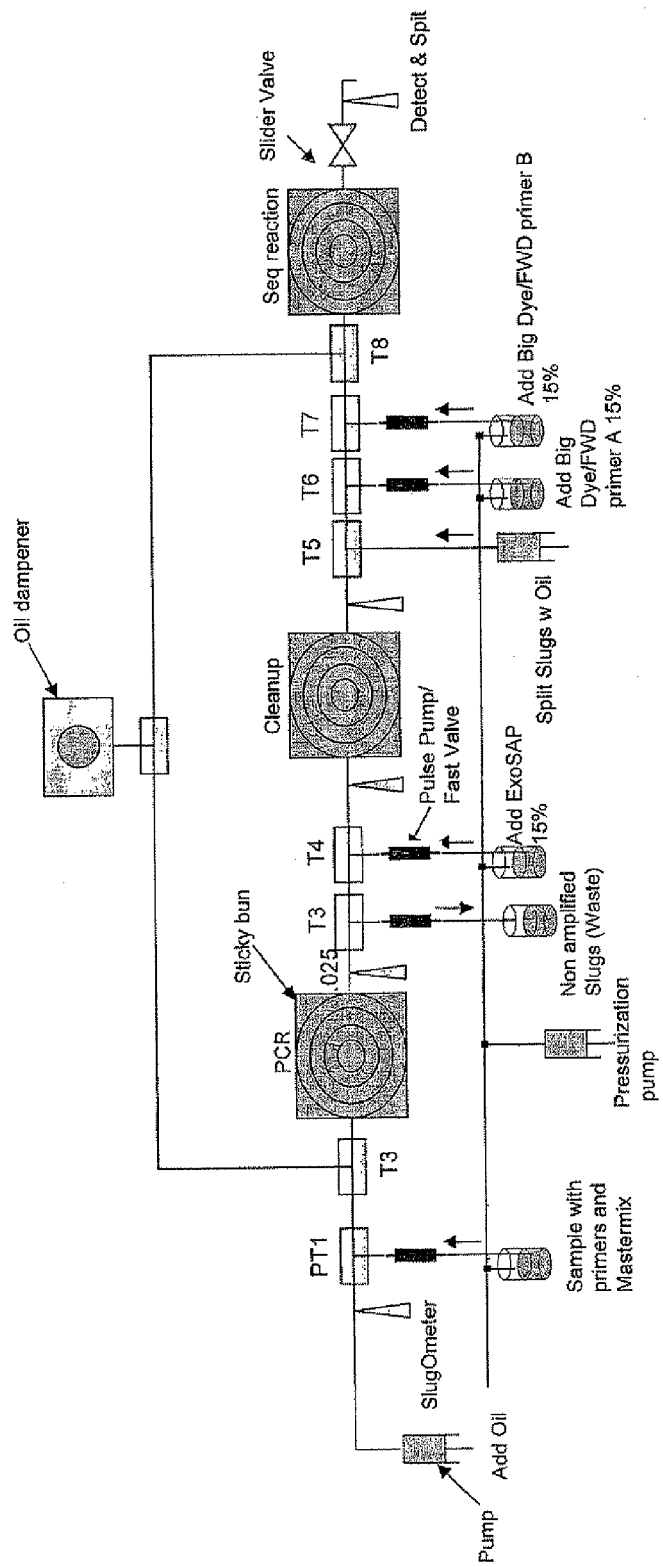

FIGS. 6, 7, and 8 depict various schematic diagrams of three respective systems according to various embodiments. Greater details about such systems and their components can be found, for example, in each of U.S. patent application Ser. No. 11/507,735, U.S. patent application Ser. No. 11/508,044, U.S. patent application Ser. No. 11/508,756, and U.S. patent application Ser. No. 11/507,733, all filed on Aug. 22, 2006, which are incorporated herein in their entireties by reference. Greater details about systems and methods for fluid manipulation that can be used in conjunction with the teachings herein, can also be found in concurrently filed U.S. Provisional Patent Application No. 60/891,208 entitled "Non Continuous Addition of Fluid to Immiscible Fluid Discrete Volumes Using an Electric Field" to Woo et al., which is incorporated herein in its entirety by reference.

In the schematic diagrams of FIGS. 6-8, the detector system (labeled SlugOmeter in the diagrams) can be the same as the various detectors shown and described in U.S. patent application Ser. No. 11/507,735, U.S. patent application Ser. No. 11/508,044, U.S. patent application Ser. No. 11/508,756, and U.S. patent application Ser. No. 11/507,733. The Big Dye/FWD primer refers to dye terminator sequencing reagents wherein each of the dideoxynucleotide chain-terminators can be labeled with a separate fluorescent dye which fluoresces at a different wavelength, for example, the BigDye® Terminator v3.1 and v1.1 product family available from Applied Biosystems, Foster City, Calif. Primer A and Primer B can be different sequencing primers known in the art, for example, forward primers, reverse primers, and zip code primers. Primer A and Primer B can be real time PCR primers known in the art, for example, cDNA primers and SNP primers. ExoSAP refers to a reagent for PCR clean-up prior to downstream sequencing comprising two enzymes, Exonucleose I and shrimp alkaline phosphatase. ExoSAP can be utilized to remove unwanted dNTPs, residual primers, and extraneous single stranded DNA from the PCR mixture.

FIGS. 9 and 10 depict various schematic diagrams of two respective systems according to various embodiments. In the system shown in FIG. 9, a sample in the form of a discrete volume, and at least one primer in the form of a discrete volume, can be separated by oil and can then be merged together by removing the oil between them. By suctioning off the oil that otherwise would space the sample discrete volume and the primer discrete volume apart, the two discrete volumes can be made to coalesce. The surge of pressure differential can be of sufficient force to cause the sample discrete volume and the primer discrete volume to merge together and coalesce even when they would not coalesce when in close proximity in the absence of such a pressure differential surge. The pressure differential can be of any adequate value to enable coalescence of the two discrete volumes. Exemplary pressure differentials can include differentials of from about 3 psi to about 25 psi, for example, from about 4 psi to about 10 psi or about 5 psi. Greater ranges of pressures will work with different diameter tubing and changes to flow resistance, among other variables.

In the system shown in FIG. 10, a sample in the form of a discrete volume, and at least one primer in the form of a discrete volume, can be separated by oil and can then be merged together by injecting and addition fluid, such as a master mix (for example, PCR master mix available from Applied Biosystems, Foster City, Calif.), between the two discrete volumes. The addition fluid can be miscible with both the sample discrete volume and the primer discrete volume. By injecting the addition fluid with a pressure differential surge between the two adjacent discrete volumes, oil that otherwise would space the sample discrete volume and the primer discrete volume apart is forced out of the way such that the two discrete volumes and the addition fluid can be made to coalesce. The surge of pressure differential can be of sufficient force to cause the sample discrete volume, the primer discrete volume, and the addition fluid to merge together and coalesce even when they would not coalesce when in close proximity in the absence of such a pressure differential surge. Several additions can be made at intervals, so that precise positioning of volume/precise time of the addition does not increase the success of the addition. The pressure differential can be of any adequate value to enable coalescence of the two discrete volumes with the addition fluid. Exemplary pressure differentials can include differentials of from about 3 psi to about 25 psi, for example, from about 4 psi to about 10 psi or about 5 psi. Valves, pumps, sizes, burst parameters, and circuitry, and control systems that can be used for controlling such injection can include those described herein, for example, in connection with the embodiments shown in FIGS. 3 and 4.

FIG. 11 is a technical drawing and specification sheet for an exemplary valve that can be used according to various embodiments.

FIG. 12 is a cross-sectional view of a system and method for splitting a discrete volume and the pressurized addition of a first reagent to the first half of the split discrete volume and the pressurized addition of a second reagent to the second half of the split discrete volume. Discrete volumes of an aqueous fluid are separated by an oil with a soluble surfactant therein, with which the aqueous fluid is immiscible. The discrete volumes 1, 2, and 3 are not uniformly spaced in the conduit. Another conduit continuously and uniformly flows more oil with surfactant into a junction of that conduit and the conduit containing the series of discrete volumes 1, 2, and 3. As the discrete volumes pass through the junction, the flow of oil with surfactant splits them into to smaller discrete volumes. In some embodiments, and as illustrated in FIG. 12, the uniform addition of oil with surfactant can split discrete volume 1 into two approximately equal halves, 1a and 1b, each a smaller discrete volume containing approximately have the volume of the original discrete volume 1. The same process occurs with discrete volumes 2 and 3, as illustrated to the right of the junction (before is illustrated to the left of the junction, after is illustrated to the right of the junction). The relevant parameters to affect whether the discrete volume is split into two, three, or more smaller discrete volumes and the relative volumes of the smaller discrete volumes can include the flow rate of the composition of discrete volumes of aqueous fluid separated by oil with surfactant and the size of the discrete volumes 1, 2, and 3.

Still in reference to FIG. 12, after splitting the discrete volumes 3 into smaller discrete volumes 3a, 3b, a discrete volume detection sensor shown below the conduit detects the presence and/or the length of smaller discrete volume 3a, and provides the information to a system controller (not shown) that predicts the time that smaller discrete volume 3a will be positioned under the forward primer conduit, so as to control the actuation of the valve and release of pressurized forward primer, which will coalesce with smaller discrete volume 3a. The system controller can also calculate the time that smaller discrete volume 3b will be positioned under the reverse primer conduit, so as to control the actuation of the valve and release of pressurized reverse primer, which will coalesce with smaller discrete volume 3b. The locations of the conduits for the forward and reverse primer reagents can be fixed as a function of the expected spacing of the smaller discrete volumes 3a and 3b with the uniform addition of oil with surfactant at a predetermined flow rate. The valves are opened for a predetermined time to allow metered amounts to be added to alternated discrete volumes 3a and 3b. In the embodiment illustrated in FIG. 12, random spacing of discrete volumes 1, 2, and 3 will not affect the volume of addition.

Figure 13:
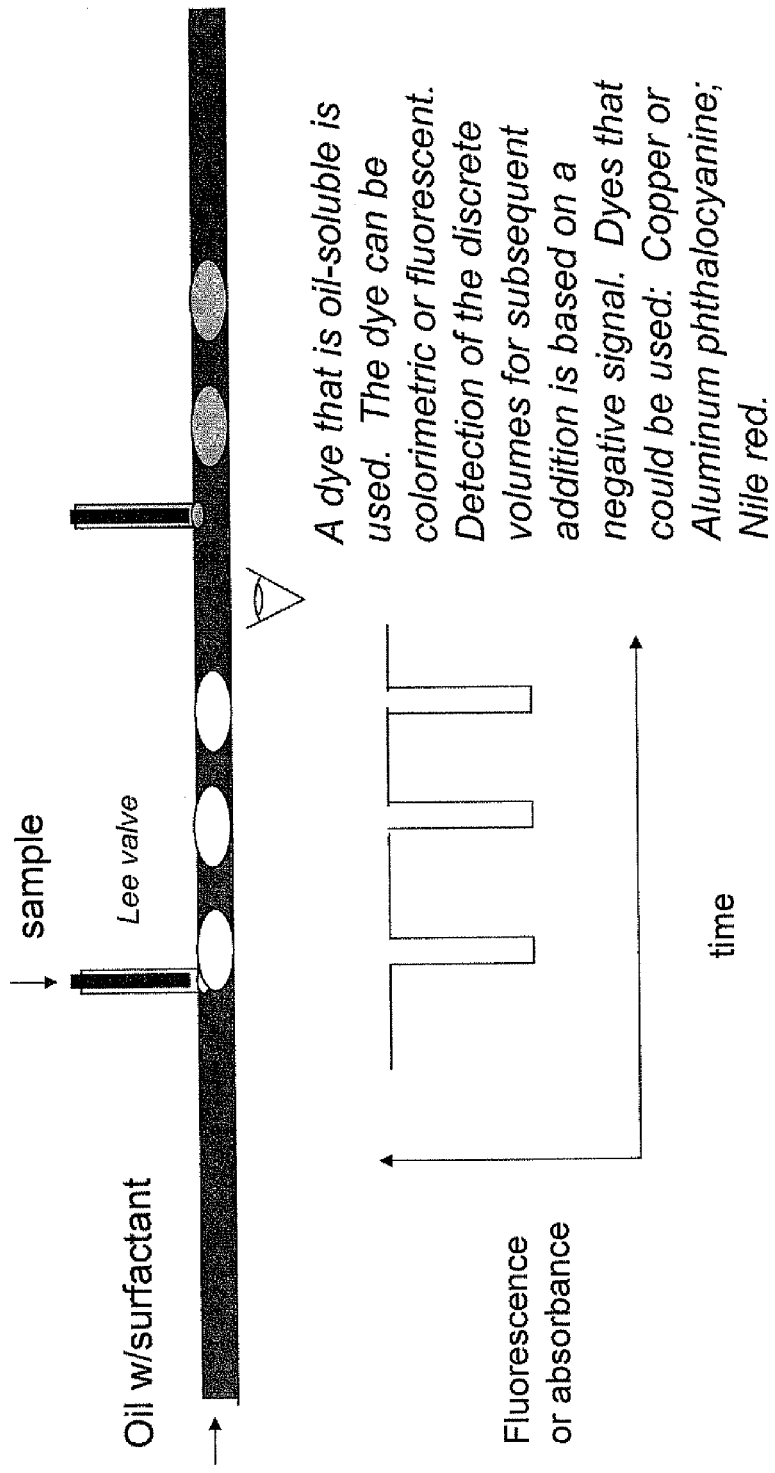
FIG. 13 is cross-sectional view of a system and method for detecting discrete volumes in a conduit.

FIG. 13 illustrates another system and method of detecting discrete volumes of a first fluid separated by a second fluid with which the first fluid is immiscible. As illustrated in FIG. 13, a dye that is soluble in the second fluid is added to the second fluid. That dye is not added to the first fluid. Therefore, a detector that detects the presence of the dye in the second fluid will sense a signal as shown in the graph: A constant higher value, with short pulses of a lower signal. In some embodiments, the dye can be colorimetric. In some embodiments, the dye can be fluorescent. Detection of the discrete volumes, as, for example, discussed in regard to FIG. 12, can use this "negative" or reduced signal to time subsequent additions of fluid that is miscible with the first fluid. In some embodiments where the second fluid is oil, exemplary dyes that can be used as described above include copper or aluminum phthalocyanine. Nile Red, for example, produced by Sigma Aldrich, dissolves in silicone oils and emits yellow light (about 560 mm) when irradiated with blue light.

In some embodiments, including the resequencing (or variable input) workflow, Nile Red cam be used in the oil phase. A blue LED detection sensor can be used for all detection sensors (labeled SlugOmeter and illustrated with a triangle in FIGS. 6 and 7) in all locations except the last one. Triggering off of the negative signal can permit timed addition of exoSAP, and later the sequencing terminators, (e.g., labeled "Big Dye/FWD primer A in FIG. 7). In some embodiments, the forward primer can have a first concentration of red dye and the reverse primer can have a second concentration of red dye, where the first and second concentrations are resolvable. Exemplary red dyes are FMAT blue from Applied Biosystems, and Cy5 from Invitrogen. In some embodiments, including those using the different concentrations of red dye in the forward and reverse primer, a "red" LED detection sensor can be used at the depositing ("spit") end of a microfluidic device to track the forward and reverse reactions.

Other embodiments of the present teachings will be apparent to those skilled in the art from consideration of the present specification and practice of the present teachings disclosed herein. It is intended that the specification and examples be considered as exemplary only and not be limiting. All cited references, patents, and patent applications are incorporated in their entireties herein by reference.

What is claimed is:
1. A system comprising:
a first conduit;
a composition in the first conduit, the composition comprising an oil and discrete volumes of an aqueous fluid in the oil, the oil and the aqueous fluid being immiscible with one another and the discrete volumes being spaced apart from one another;
a second conduit in fluid communication with the first conduit, at a junction, wherein the second conduit contains an oil;
a valve disposed along the second conduit wherein the valve is configured to be actuated for a period between 0.1 milliseconds to about 10 milliseconds, a blue LED detector;
a volume detection sensor configured to the detect the length of each discrete volume of aqueous fluid; and
a control system associated with the valve and configured to:
open the valve when one of the discrete volumes is present at the junction,
determine a flow rate of the discrete volumes of aqueous fluid, and
determine a pressure and volume of oil to inject into the discrete volume of aqueous fluid, wherein the system is configured to segment a discrete volume of aqueous fluid by opening the valve and injecting oil located in the second conduit into the first conduit.

2. The system of claim 1, wherein the valve comprises a solenoid valve.

3. The system of claim 1, further comprising a pump associated with the valve, wherein the control system is configured to actuate the valve and power the pump.

4. The system of claim 3, wherein the circuitry is programmed to actuate the valve, from a non-actuated position, one or more times within a 100 millisecond period, upon a triggering event.

5. The system of claim 4, wherein the triggering event comprises a detection of one of the discrete volumes at or near the junction.

6. A system comprising:
a first conduit;
a composition in the first conduit, the composition comprising an oil and discrete volumes of an aqueous fluid in the oil, the oil and the aqueous fluid being immiscible with one another and the discrete volumes being spaced apart from one another;
a second conduit in fluid communication with the first conduit, at a junction, wherein the second conduit contains an oil;
a valve disposed along the second conduit,
a blue LED detector; and
a pump configured to pump a liquid through the second conduit and configured to provide multiple bursts of pressure within a 100 millisecond period,
a volume detection sensor configured to the detect the length of each discrete volume of aqueous fluid; and
a control system associated with the valve and configured to:
open the valve when one of the discrete volumes is present at the junction,
determine a flow rate of the discrete volumes of aqueous fluid, and
determine a pressure and volume of oil to inject into the discrete volume of aqueous fluid,
wherein the system is configured to segment a droplet by opening the valve and injecting oil located in the second conduit into the first conduit.

7. A system comprising:
a first conduit;
an oil in the first conduit;
a second conduit in fluid communication with the first conduit, at a junction;
an aqueous fluid in the second conduit, the oil and the aqueous fluid being immiscible with one another;
a valve disposed along the second conduit a blue LED detector; and
a volume detection sensor configured to the detect the length of each discrete volume of aqueous fluid
a fluid movement system configured to:
open the valve and force portions of the aqueous fluid from the second conduit into the first conduit to form discrete volumes of the aqueous fluid spaced apart from one another, in the oil,
determine a flow rate of the discrete volumes of aqueous fluid, and
determine a pressure and volume of oil to inject into the discrete volume of aqueous fluid,
wherein the system is configured to segment a droplet by opening the valve and introducing aqueous fluid located in the second conduit into the first conduit,
wherein the flow of oil in the first conduit is configured to segment the aqueous fluid entering the first conduit.

8. The system of claim 7, wherein the fluid movement system comprises one or more pumps, at least one of the one or more pumps is configured to pump the aqueous fluid through the second conduit at a predetermined rate, and the valve is configured to be actuated for a period of time based on the rate to provide discrete volumes of a pre-selected volume.

* * * * *